United States Patent [19]
Reinehr et al.

[11] Patent Number: 6,096,919
[45] Date of Patent: Aug. 1, 2000

[54] PROCESS FOR THE PREPARATION OF SULPHONATED DISTYRYL-BIPHENYL COMPOUNDS

[75] Inventors: Dieter Reinehr, Kandern, Germany; Georges Metzger, Moernach; Fabienne Cuesta, Roppentzwiller, both of France; Denis Planchenault, Lausanne; Eric Signoret, Les Giettes, both of Switzerland

[73] Assignee: Ciba Specialty Chemicals Corporation, Tarrytown, N.Y.

[21] Appl. No.: 09/309,232

[22] Filed: May 10, 1999

[30] Foreign Application Priority Data

May 13, 1998 [EP] European Pat. Off. ............. 98810432

[51] Int. Cl.[7] .................................................. C07C 247/00
[52] U.S. Cl. .................. 562/87; 8/552; 427/158
[58] Field of Search ................................ 562/87; 568/635

[56] References Cited

U.S. PATENT DOCUMENTS

| | | | |
|---|---|---|---|
| 3,907,904 | 9/1975 | Luethi . | |
| 3,984,399 | 10/1976 | Weber et al. | 260/240 |
| 4,013,642 | 3/1977 | Meyer | 260/240 |
| 4,118,560 | 10/1978 | Weber . | |
| 4,231,957 | 11/1980 | Märky | 260/505 |
| 5,332,861 | 7/1994 | Guglielmetti | 562/87 |
| 5,622,749 | 4/1997 | Rohringer et al. | 427/158 |
| 5,830,241 | 11/1998 | Rohringer et al. | 8/552 |

OTHER PUBLICATIONS

Advances in Heterocyclic Chemistry, vol. 23, pp. 171–185, 1978.

King et al., Canadian Journal of Chemistry, vol. 49, (1971), pp. 936–942.

*Primary Examiner*—Ardin H. Marschel
*Assistant Examiner*—Sherif Kafafi
*Attorney, Agent, or Firm*—Kevin T. Mansfield

[57] ABSTRACT

A process for the preparation of sulphonated distyryl-biphenyl compounds of formula:

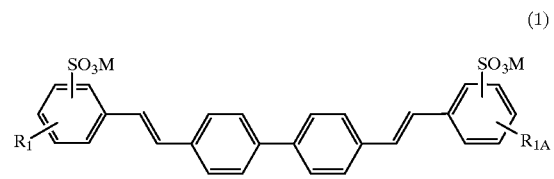

in which $R_1$ represents hydrogen, $C_1$–$C_5$ alkyl, $C_1$–$C_5$ alkoxy or halogen, $R_{1A}$ represents hydrogen, $C_1$–$C_5$ alkyl, $C_1$–$C_5$ alkoxy or halogen and M represents hydrogen, an alkaline- or alkaline earth-metal, or ammonium, characterised by reacting a compound of formula:

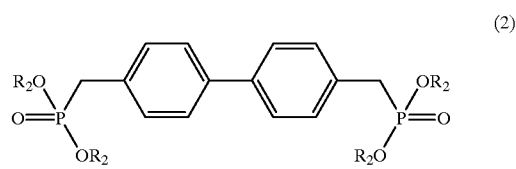

in which $R_2$ represents $C_1$–$C_5$ alkyl, with a compound of formula:

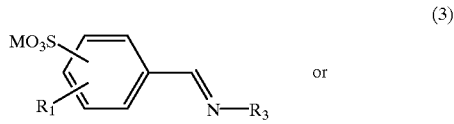

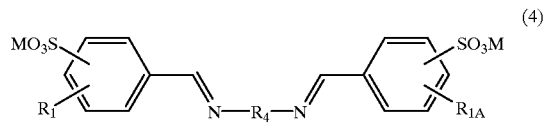

whereby $R_3$ represents phenyl, optionally substituted by $C_1$–$C_4$ alkoxy, halogen or $SO_3M$, or $C_1$–$C_{12}$ alkyl, $R_4$ represents $C_2$–$C_6$ alkylene, and M, $R_1$ and $R_{1A}$ are defined as above, in an alcoholic or dipolar aprotic solvent and in the presence of a strong base. Novel compounds of formulae (3) and (4) and a process for their preparation.

16 Claims, No Drawings

PROCESS FOR THE PREPARATION OF SULPHONATED DISTYRYL-BIPHENYL COMPOUNDS

The present invention relates to a new process for the preparation of sulphonated distyryl-biphenyl compounds, new sulphonated imine intermediates therefore and a process for the preparation of said intermediates.

A number of processes for the preparation of sulphonated distyryl-biphenyl compounds have previously been described. Thus, for example, U.S. Pat. No. 3,984,399 describes the reaction of 4,4'-bis (dimethoxyphosphonomethyl)-biphenyl with benzaldehyde-2-sulphonic acid, whilst CH 505036 describes reaction of sulphonated benzaldehydes with bis-phosphine oxides of biphenyl as well as reaction of biphenyl-4,4'-dialdehyde with correspondingly substituted aryl phosphine oxides. U.S. Pat. No. 4,231,957 further describes the stepwise reaction of two different aromatic aldehydes with bis-phosphonium salts of biphenyl, thus yielding asymmetric derivatives.

The success of these processes depends, to a very great extent, on both the availability of the required benzaldehydes and on their stability under the reaction conditions necessary for condensation. In certain cases it has been found that the required benzaldehydes can either only be obtained in poor yields or are not readily isolable when their availability is required on an industrial scale.

Surprisingly, it has now been found that readily available sulphonated imines react readily with 4,4'-bis-(alkoxyphosphonomethyl)-biphenyl to give sulphonated distyryl-biphenyl compounds in excellent yield and purity.

Correspondingly, the subject of the present invention is a process for the preparation of sulphonated distyryl-biphenyl compounds of formula:

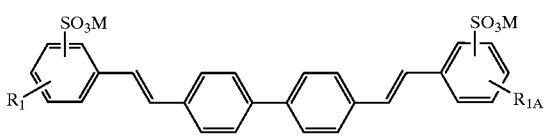
(1)

in which $R_1$ represents hydrogen, $C_1$–$C_5$ alkyl, $C_1$–$C_5$ alkoxy or halogen, $R_{1A}$ represents hydrogen, $C_1$–$C_5$ alkyl, $C_1$–$C_5$ alkoxy or halogen and M represents hydrogen, an alkaline- or alkaline earth-metal, or ammonium, characterised by reacting a compound of formula:

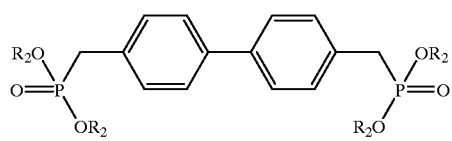
(2)

in which $R_2$ represents $C_1$–$C_5$alkyl, with a compound of formula:

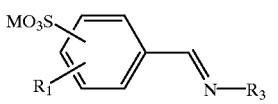
(3)

or

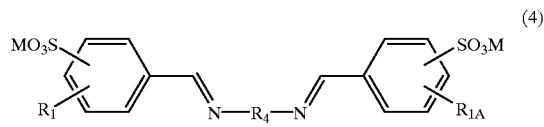
(4)

whereby $R_3$ represents phenyl, optionally substituted by $C_1$–$C_4$alkoxy, halogen or $SO_3M$, or $C_1$–$C_{12}$alkyl, $R_4$ represents $C_2$–$C_6$alkylene or phenylene, and M, $R_1$ and $R_{1A}$ are defined as above, in an alcoholic or dipolar aprotic solvent and in the presence of a strong base.

As alkyl groups of $C_1$–$C_{12}$ atoms there may be defined methyl, ethyl, any of the isomers of propyl, butyl, pentyl, hexyl, heptyl, octyl, nonyl, decyl undecyl or dodecyl groups. $C_1$–$C_5$ alkoxy groups may be methoxy, ethoxy, n- or isopropoxy, n-, sec-, or t-butoxy, n-pentyloxy, iso-amyloxy or sec-amyloxy groups and halogen may be fluorine, chlorine, bromine, or iodine, preferably chlorine. $C_2$–$C_6$alkylene groups may be ethylene, propylene, butylene, pentylene or hexylene, preferably ethylene, propylene or butylene. When M represents an alkaline or alkaline earth metal these are preferably Li, Na or K, or Ca or Mg, whilst when M represents ammonium these may be $NH_4$, mono-, di-, tri- or tetramethylammonium, mono-, di-, tri- or tetraethylammonium, mono, di-, tri- or tetra-n- or isopropylammonium, mono, di-, tri- or tetra-n-, sec- or t-butylammonium, mono-, di- or triethanolammonium, mono-, di- or tri-n- or isopropanolammonium, mono-, di- or tri-n- sec- or t-butanolammonium, morpholinium, piperidinium or pyrrolidinium.

The process is particularly suitable for preparation of the compounds of formula (1) in which $R_1$ and $R_{1A}$ both represent hydrogen or chlorine and M represents H, K or Na and most especially for a compound of formula:

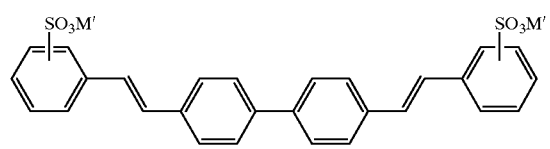
(5)

in which M' represents potassium or sodium.

The bis-phosphonomethyl compounds of formula (2) are obtained by reacting 4,4'-bis-chloromethyl biphenyl with a trialkyl phosphite, preferably trimethyl or triethyl phosphite, When the solvent used in the process is an alcohol, this is preferably methyl, ethyl propyl or butyl alcohol, whilst as dipolar aprotic solvent dimethylformamide, dimethylacetamide, dimethylsulphoxide or N-methylprrolidine or mixtures thereof are preferred.

The strong base used in the process may be sodium or potassium hydride, sodium or potassium hydroxide, or the sodium or potassium salt of $C_1$–$C_5$ alcohol or mixtures thereof, preferably mixtures of sodium methylate and potassium-t-butylate.

The temperature at which the process is performed may vary over a wide range, for example, from about 20° C. to about 120° C., but is preferably within the range of from about 50° C. to about 100° C.

In a second aspect, the invention is directed towards a process for the preparation of sulphonated distyryl-biphenyl compounds of formula (1), or mixtures thereof, characterised by hydrolysing one or more compounds of formula (3) to produce one or more benzaldehydes of the formula:

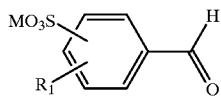

(6)

wherein M and $R_1$ are defined as above, which is reacted with a compound of formula (2) in an aprotic solvent, in the presence of a strong base.

The aprotic solvent used in the above-described process may be an aromatic solvent, for example, benzene, toluene, xylene, a chlorobenzene or preferably a cyclic or linear amide such as N-methylpyrrolidone, dimethylformamide, diethylformamide or dimethylacetamide, or a sulphoxide such as dimethylsulphoxide.

Suitable strong bases are alkali metal hydroxides, amides and alcoholates. Particularly suitable are the lithium, sodium or potassium alcoholates containing 1–5 carbon atoms.

In principle the reaction temperature can vary from 10° C. to the boiling point of the solvent utilised, although it is generally advantageous to carry out the reaction within a temperature range of 30° to 60° C.

The solvent used in the hydrolysis of compounds of formula (3) are esters, ethers or water. Suitable esters include n-Butyl acetate, Isobutyl acetate, Ethyl acetate, Isobutyl isobutyrate, n-Propyl acetate and Isopropyl acetate. Suitable ethers include Isopropyl Ether, Tetrahydrofuran, Dioxane and Diethyl ether. The preferred solvent is water.

The hydrolysing agent used include dilute solutions of a sulfuric acid or hydrochloric acid. Preferred hydrolysing agents are dilute solutions of acids of the formula (3):

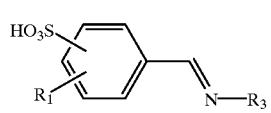

(3)

wherein $R_1$ and $R_3$ are defined as above.

The temperature at which the hydrolysis is performed may vary over a range of from about 0° C. to about 100° C., but is preferably within the range of from about 20° C. to 40° C.

Of particular importance is the following mixture of sulphonated distyryl biphenyl compounds, 50% compound A, 25% compound B and 25% compound C, produced by the above process:

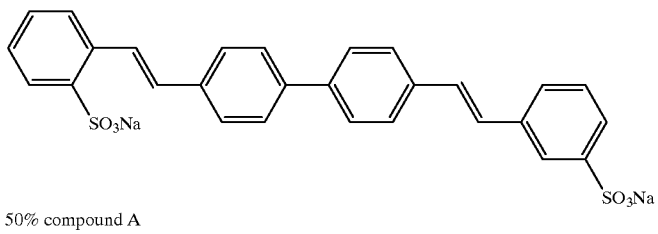

50% compound A

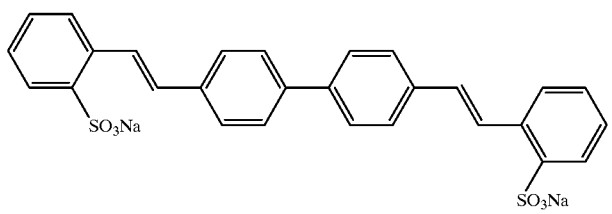

25% compound B

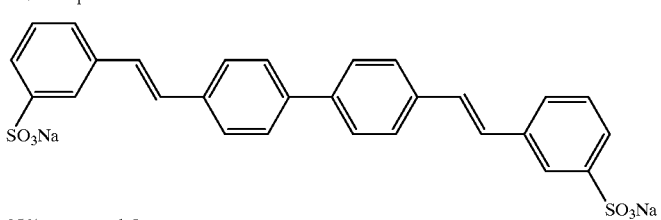

25% compound C

In a third aspect, the invention is directed towards novel imines of the formula

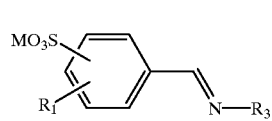

(3)

in which $R_3$ represents $C_1$ to $C_{12}$ alkyl or a radical of the formula

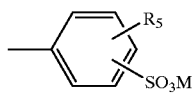

whereby $R_5$ is hydrogen, halogen or $C_1$ to $C_4$ alkoxy, and $R_1$ and M are as previously defined as well as a process for the their preparation which comprises reacting a compound of formula:

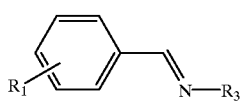

(7)

in which $R_1$ and $R_3$ are as previously defined, with a sulphonating agent.

In one preferred embodiment, the imines are of the formula:

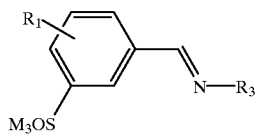

(8)

in which $R_3$ represents $C_1$ to $C_{12}$ alkyl or a radical of the formula

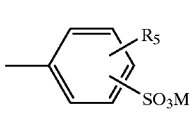

(9)

whereby $R_5$ is hydrogen, halogen or $C_1$ to $C_4$ alkoxy, and $R_1$ and M are as previously defined.

In another preferred embodiment, the imines of formula (3) are those whereby $R_3$ is a $C_1$–$C_4$ alkyl group.

In a fourth aspect, the invention is directed towards novel imines of the formula

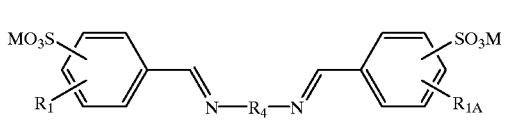

(4)

in which $R_1$, $R_{1A}$, $R_4$ and M are as previously defined as well as a process for the their preparation which comprises reacting a compound of formula:

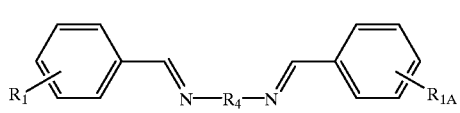

(10)

in which $R_1$ and $R_4$ are as previously defined, with a sulphonating agent.

As sulphonating agent for the conversion of compound (7) to (3) and of compound (10) to (4) concentrated sulphuric acid, chlorosulphonic acid, sulphur trioxide, sulphur trioxide in organic solvents, liquid sulphur dioxide and oleum or mixtures thereof may be employed, 25% oleum being especially preferred.

In dissolved or finely divided states, the sulphonated distyryl-biphenyl compounds prepared by the process of the invention display a more or less pronounced fluorescence. They are therefore used, according to the invention, for optically brightening synthetic or natural organic materials.

Examples of such materials which may be mentioned, without the review given below being intended to express any limitation thereto, are textile fibres from the following groups of organic materials, insofar as optical brightening thereof enters into consideration:

(a) Polyamides which are obtainable as polymerisation products by ring opening, for example those of the polycaprolactam type, (b) polyamides which are obtainable as polycondensation products based on bifunctional or polyfunctional compounds capable of undergoing a condensation reaction, such as hexamethylenediamine adipate and (c) natural textile organic materials of animal or vegetable origin, for example based on cellulose or proteins, such as cotton or wool, linen or silk.

The organic materials to be optically brightened can be in diverse stages of processing and are preferably finished textile products. They can, for example be in the form of hank goods, textile filaments, yarns, twisted yarns, nonwovens, felts, textile fabrics, textile composites or knitted fabrics.

The brighteners defined above are of particular importance for the treatment of textile fabrics. The treatment of textile substrates is advantageously carried out in an aqueous medium in which the particular optical brighteners are present in a finely divided form (suspensions, so-called microdispersions and in some cases solutions). Dispersing agents, stabilisers, wetting agents and further auxiliaries can optionally be added during the treatment.

The treatment is usually carried out at temperatures of from about 20° to 140° C., for example at the boiling point of the bath, or in the region thereof (about 90° C.). For the finishing, according to the invention, of textile substrates it is also possible to use solutions or emulsions in organic solvents, as are used in dyeing practice in so-called solvent dyeing (pad-thermofix method and the exhaustion dyeing process in dyeing machines).

The optical brighteners which can be used according to the present invention can also be employed, for example, in the following use forms:

(a) In mixtures with so-called "carriers", wetting agents, softeners, swelling agents, antioxidants, light stabilisers, heat stabilisers and chemical bleaching agents (chlorite bleach and bleaching bath additives).

(b) In mixtures with crosslinking agents and finishing agents (for example starch or synthetic finishing agents) and also in combination with very diverse textile finishing processes, especially synthetic resin finishes (for example crease resistant finishes such as "wash-and-wear", "permanent press" and "no-iron"), and also flame resistant finishes, soft handle finishes, anti-soiling finishes or anti-static finishes or antimicrobial finishes.

(c) As additives to various soaps and washing agents.

(d) In combination with other substances having an optical brightening action.

If the brightening process is combined with textile treatment or finishing methods, the combined treatment can in many cases advantageously be effected with the aid of corresponding stable formulations which contain the compounds having an optical brightening action in a concentration such that the desired brightening effect is obtained.

In certain cases, the full effect of the brightener is achieved by an after-treatment. This can be, for example, a chemical treatment (for example acid treatment), a thermal treatment (for example heat) or a combined chemical/heat treatment.

The amount of the optical brighteners to be used according to the invention, relative to the material to be optically brightened, can vary within wide limits. A distinct and durable effect can already be achieved with very small amounts and in certain cases, for example, with amounts of 0.03% by weight. However amounts of up to about 0.5% by weight can also be used. For most cases of interest in practice, amounts of between 0.05 and 0.5% by weight relative to the material to be brightened, are preferably of interest.

The optical brighteners are also especially suitable as additives for washing baths or to industrial and household washing agents and they can be added in various ways. They are appropriately added to washing baths in the form of their solutions in water or organic solvents or also in a state of fine division as aqueous dispersions or slurries. They, or their components, are advantageously added to household or industrial washing agents at any phase of the manufacturing process of the washing agent, for example to the so-called "slurry" prior to spray-drying of the washing powder or during the preparation of liquid washing agent combinations. The compounds can be added both in the form of a solution or dispersion in water or other solvents and also without auxiliaries in the form of a dry brightener powder. However, they can also be sprayed, in the dissolved or pre-dispersed form, onto the finished washing agent.

Washing agents which can be used are the known mixtures of detergent substances, such as, for example, soap in the form of chips and powders, synthetic products, soluble salts of sulphonic acid half-esters of higher fatty alcohols, arylsulphonic acids, which are substituted by higher alkyl and/or polysubstituted by alkyl, carboxylic acid esters with alcohols of medium to higher molecular weight, fatty acid acylaminoalkyl- or aminoaryl-glycerol-sulphonates, phosphoric acid esters of fatty alcohols and the like. So-called "builders" which can be used are, for example, alkali metal polyphosphates and alkali metal polymeta-phosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediamine-tetraacetic acid and foam stabilisers, such as alkanolamides of higher fatty acids. Furthermore, the washing agents can contain, for example: antistatic agents, superfatting skin protection agents, such as lanolin, enzymes, antimicrobial agents, perfumes and dyestuffs.

The brighteners have the particular advantage that they are also effective in the presence of active chlorine donors, such as, for example, hypochlorite and can be used without substantial loss of the effects in washing baths with non-ionic washing agents, for example alkylphenol polyglycol ethers. Also in the presence of perborate or peracids and activators, for example tetraacetylglycoluril or ethylenediamine-tetraacetic acid are the new brighteners very stable both in pulverulent washing agent and in washing baths.

The brighteners according to the invention are added in amounts of 0.005 to 2% or more and preferably of 0.03 to 0.5%, relative to the weight of the liquid or pulverulent ready-to-use washing agent. When they are used to wash textiles made of cellulose fibres, polyamide fibres, cellulose fibres with a high grade finish, wool and the like, wash liquors which contain the indicated amounts of the optical brighteners according to the invention impart a brilliant appearance in daylight.

The washing treatment is carried out, for example, as follows:

The indicated textiles are treated for 1 to 30 minutes at 5° to 100° C. and preferably at 25° to 100° C. in a wash bath which contains 1 to 10 g/kg of a composite washing agent containing builders and 0.05 to 1% relative to the weight of the washing agent, of the brighteners claimed. The liquor ratio can be 1:3 to 1:50. After washing, the textiles are rinsed and dried in the customary manner. The wash bath can contain, as a bleach additive, 0.2 g/l of active chlorine (for example in the form of hypochlorite) or 0.1 to 2 g/l of sodium perborate.

The brighteners according to the invention can also be applied from a rinsing bath with a "carrier". For this purpose the brightener is incorporated in a soft rinsing agent or in another rinsing agent, which contains, as the "carrier", for example, polyvinyl alcohol, starch, copolymers on an acrylic basis or formaldehyde/urea or ethylene-urea or propylene-urea derivatives, in amounts of 0.005 to 5% or more and preferably of 0.2 to 2%, relative to the rinsing agent. When used in amounts of 1 to 100 ml, and preferably of 2 to 25 ml, per litre of rinsing bath, rinsing agents of this type, which contain the brighteners according to the invention, impart brilliant brightening effects to very diverse types of treated textiles.

A further application of the compounds of the invention is for the brightening of paper, either in the pulp mass during paper manufacture or in the size-press, which has been described in British Patent Specification 1,247,934, or preferably in coating compositions. Such coating compositions utilising certain distyryl-biphenyl optical brighteners have been described in British Patent Specification 2,277,749 in considerable detail. When brighteners prepared by the process of the present invention are employed in such formulations papers brightened with them exhibit a very high degree of whiteness.

The following Examples serve to illustrate the invention; parts and percentages are by weight, unless otherwise stated.

(101)

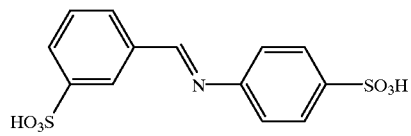

7.2 g of benzalaniline (Beilstein 12, p. 195) are added in portions to 64 g of 25% oleum, whereby the temperature rises to 85° C. The reaction mass is then heated to 150° C. and stirred at this temperature for a further 20 minutes. The liquid reaction mixture is then poured into 950 ml of ethyl acetate, stirred for 1 hour at room temperature, filtered and washed. After drying in a desiccator, there are obtained 13.66 g of compound (101) as a white powder melting at 296–298° C. with decomposition.

Analysis for $C_{13}H_{11}NO_6S_2.0.75\ H_2O$: calculated: C 44.00%, H 3.48%, N 3.95%, S 18.08%; found: C 44.02%, H 3.52%, N 3.69%, S 17.65%

The structural formula was confirmed by H-NMR spectroscopy

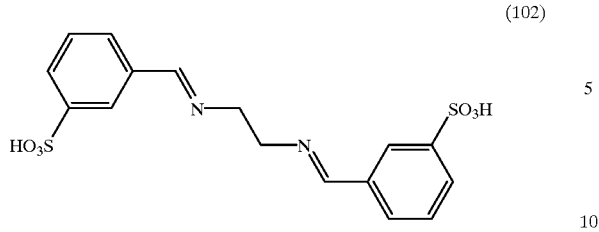
(102)

4.72 g of bis-benzalethylenediamine (Beilstein 7, p. 214) is added to 50 g of 25% oleum, the mixture heated to 150° C. and stirred for a further 45 minutes at this temperature. After cooling, the mixture was added to ethyl acetate and treated as described in Example 1. There are obtained 11.2 g of compound (102)

Analysis for $C_{16}H_{16}N_2O_6S_2 \cdot 1.7\ H_2SO_4$: calculated: C 34.12%, H 3.47%, N 4.97%, S 21.00%; found C 34.50%, H 3.60%, N 4.70%, S 20.50%;

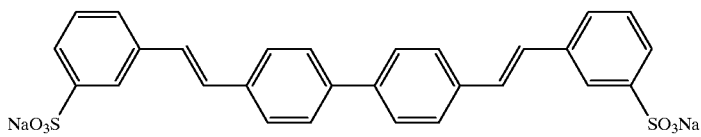
(103)

4.43 g of compound (101) and 2.05 g of 4,4'-bis-(dimethoxyphophonomethyl)-biphenyl are dissolved in 50 ml of dimethylsulphoxide. After the addition of 0.6 g of potassium tertiary butylate and 8.3 g of a 30% methanolic sodium methylate solution, the mixture is heated at 80° C. for 45 minutes and then 400 ml of acetone are added. The precipitated solid is filtered and the sulphanilic acid removed by treatment with methanol/water. After purification, 2.2 g of the compound of formula (103) are obtained.

Analysis for $C_{28}H_{20}Na_2O_6S_2 \cdot 2.5\ H_2O$: calculated: C 55.35%, H 4.14%, N 10.56%, S 7.40%; found: C 55.40%, H 4.10%, N 10.42%, S 7.16%;

EXAMPLE 4

3.55 g of compound (102) and 2.05 g of 4,4'-bis-(dimethoxyphophonomethyl)-biphenyl are dissolved in 50 ml of dimethylsulphoxide. After the addition of 0.6 g of potassium tertiary butylate and 18.8 g of a 30% methanolic sodium sodium methylate solution, the mixture is heated at 80° C. for 45 minutes and then 500 ml of acetone are added. The precipitated solid is filtered and dried to yield 2.28 g of the compound of formula (103).

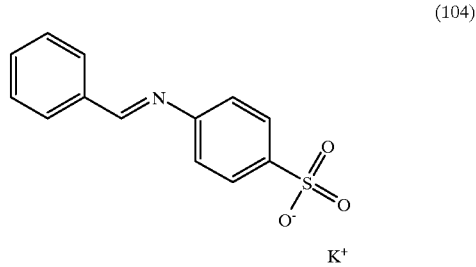
(104)

To a solution of 7.42 g of sulfanilic acid potassium salt (0.04285 mol) and 15 ml water, is added 5.05 g of benzaldehyde (0.04713 mol). This mixture is stirred and heated at 20° C. After 2 minutes, a white solid precipitates and the temperature is raised to 27° C. The reaction mass is cooled to 0° C., filtered, washed and dried to give 11 g (75% yield) of the compound of formula (104).

The structural formula was confirmed by H-NMR spectroscopy:

$^1$H-NMR Spectrum: δ(ppm):7.25(d), 7.6(m), 7.7(d), 8.0 (d), 8.7(s) in a ratio of 2:3:2:2:1

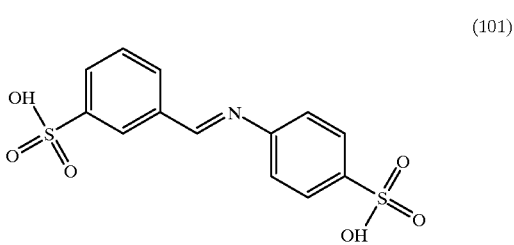
(101)

A mixture of 2 g (0.0066 mol) of compound (104) and 7 g of 30% Oleum (0.0265 mol) is heated to 130° C. (bath temperature) and stirred for 3 hours. To the reaction solution 150 ml of ethyl acetate is added. The precipitated solid is filtered and washed. There are obtained 2.5 g of compound (101).

(105)

To 25% oleum (63 g; 0.197 mol) is slowly added warm (80° C.) liquid benzylidene phenyl amine (54.4 g; 0.3 mol) then a 66% solution of oleum in sulphuric acid (105.1 g; 0.867 mol) is slowly added to the mixture (temperature is controlled during addition). The mixture is then stirred at 110° C. for 6 hours, cooled to room temperature then poured in water (300 g). Sulphanilic acid is filtered, washed with water and dried. Mother liquor and wash liquor are then neutralised (pH 3) with a solution of 50% NaOH. Water is distilled and the residue is poured into dimethylformamide (250 g). Sodium sulfate is filtered and washed with dimethylformamide. The dimethylformamide solution is finally partially distilled to get 350 g of a 14.1% compound (105)/dimethylformamide solution (yield: 79%).

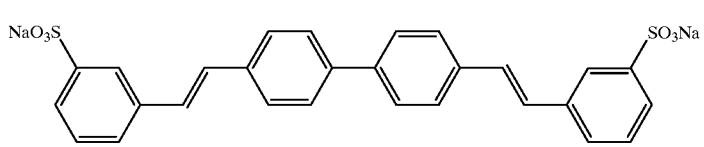

(103)

To a mixture of methyl diphenylphosphonate 88% (22.6 g; 0.05 mol) and a solution of compound (105) in dimethylformamide (260.3 g 8.1%; 0.102 mol) at 45° C. under 30 mbar is slowly added to 27 g (0.2 mol) of a 30% methanolic sodium methylate solution. After addition, the reaction mixture is stirred at 45° C. under 30 mbar for 3 hours then neutralised with sulphuric acid (0.55 g, pH 3). Dimethylformamide is distilled and the resulting solid is poured into boiling distilled water (150 g) and stirred for 20 minutes. The solid is filtered under pressure then washed with boiling distilled water (150 g) and filtered again. The solid is finally dried for 12 h (100° C., 30 mbar) to give the pale yellow compound (103), (27.2 g, with a purity of 72%) (yield; 70%).

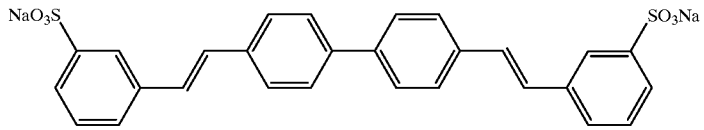

To 4.43 g (0.012 mol) of the compound (101) are added 1.2 g of hydrochloric acid 37% (0.012 mol). To this mixture are added 2.26 g of methyl diphenylphosphonate 88% (0.005 mol) and 50 ml of dimethylformamide. This mixture is slowly added to a solution of 8.3 g (0.046 mol) of a 30% methanolic sodium methylate solution. After addition, the reaction mixture is stirred at 80° C. under 30 mbar for 3 hours. A yellow solid is precipitated during this process. After cooling at 25° C. the solid is filtered, then washed twice with 5 ml of dimethylformamide then with 10 ml of acetone. Compound (103) is finally dried for 12 h (80° C., 30 mbar) to give a pale yellow solid (2.0 g; 0.036 mol), with a purity of 95% (yield; 76%).

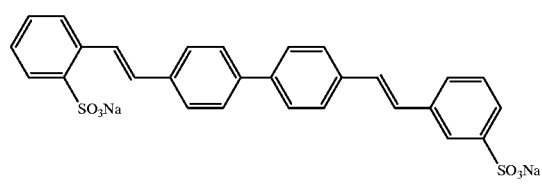

50% compound A

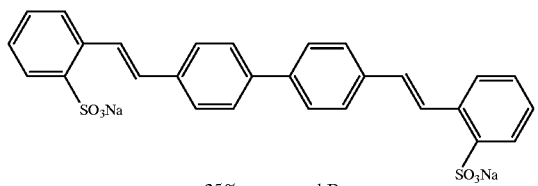

25% compound B

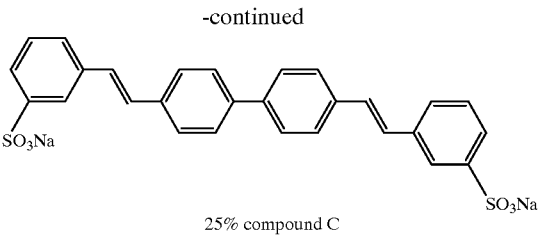

25% compound C

To a mixture of methyl diphenylphosphonate 88% (17.5 g; 0.039 mol) and a 4.5% solution of ortho-formylsulfonic acid, sodium salt (251.3 g; 0.0485 mol) in dimethylformamide at 45° C. under 30 mbar is slowly (5–10 minutes) added 8 g (0.06 mol) of a 30% methanolic sodium methylate solution. After addition, the reaction mixture is stirred at 45° C. under 30 mbar for 2 hours then compound (105)/dimethylformamide (11.85 g at 79.9%; 0.044 mol) is added to the mixture at 45° C. under nitrogen. To this resulting mixture is added, at 45° C. under 30 mbar, 8 g (0.06 mol) of a 30% methanolic sodium methylate solution. Then the reaction mixture is stirred at 45° C. under 30 mbar for 5 hours and neutralised with formic acid 100% (2 ml, pH 7). Dimethylformamide is distilled (Max 100° C.), then the resulting solid is poured into boiling distilled water (500 g) and stirred for 15 minutes at 90° C. Then 55 g of sodium chloride is slowly added at 90° C. and the reaction mixture is slowly cooled to 25° C. over a period of 3 hours. After addition of another portion of 55 g sodium chloride at 35° C., the resulting solid is filtered under pressure then washed with 150 g of a sodium chloride solution (20% in water). Finally the solid is dried for 12 h (80° C., 30 mbar) to give a pale yellow solid (25 g, with a purity of 76%) (yield; 85%). HPLC analysis shows a mixture of about 50% compound A, 25% compound B and 25% compound C.

What is claimed is:

1. A process for the preparation of sulphonated distyrylbiphenyl compounds of formula:

(1)

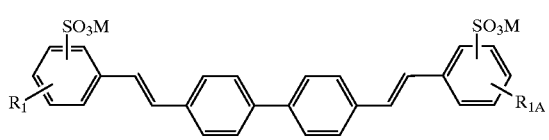

in which $R_1$ represents hydrogen, $C_1$–$C_5$ alkyl, $C_1$–$C_5$ alkoxy or halogen, $R_{1A}$ represents hydrogen, $C_1$–$C_5$ alkyl, $C_1$–$C_5$ alkoxy or halogen, and M represents hydrogen, an alkaline- or alkaline earth-metal, or ammonium, which comprises reacting a compound of formula:

(2)

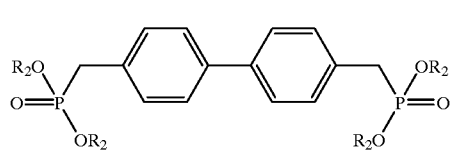

in which $R_2$ represents $C_1$–$C_5$alkyl, with a compound of formula:

(3)

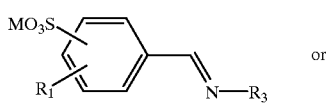

or (4)

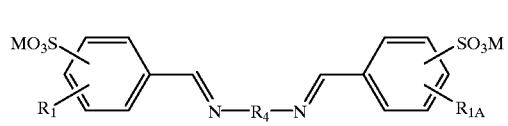

whereby $R_3$ represents phenyl, optionally substituted by $C_1$–$C_4$alkoxy, halogen or $SO_3M$, or $C_1$–$C_{12}$alkyl, $R_4$ represents $C_2$–$C_6$alkylene or phenylene, and M, $R_1$ and $R_{1A}$ is defined as above, in an alcoholic or dipolar aprotic solvent and in the presence of a strong base.

2. A process according to claim 1 in which $R_1$ and $R_{1A}$ both represent hydrogen or chlorine and M represents hydrogen, potassium or sodium.

3. A process according to claim 1 in which $R_2$ represents methyl or ethyl, $R_3$ represents phenyl, chlorophenyl or $C_1$–$C_6$alkyl or $C_2$–$C_4$alkylene.

4. A process according to claim 1 in which the solvent is a $C_1$–$C_4$ alcohol, dimethylformamide, dimethylacetamide, dimethylsulphoxide or N-methylpyrrolidone or mixtures thereof.

5. A process according to claim 1 in which the strong base is sodium or potassium hydride, sodium or potassium hydroxide or the sodium or potassium salt of a $C_1$–$C_5$ alcohol or mixtures thereof.

6. A process according to claim 1 in which the reaction is carried out at a temperature of from about 20° C. to about 120° C.

7. A process according to claim 1 for the preparation of a compound of formula:

(5)

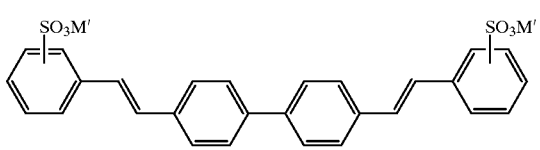

in which M' represents potassium or sodium.

8. A process for the preparation of sulphonated distyrylbiphenyl compounds of formula (1) or mixtures thereof, (1)

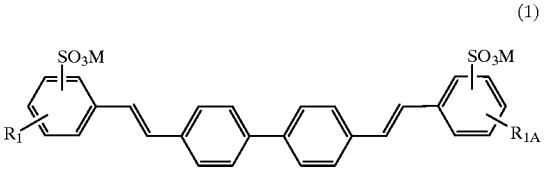

in which $R_1$ represents hydrogen, $C_1$–$C_5$ alkyl, $C_1$–$C_5$ alkoxy or halogen, $R_{1A}$ represents hydrogen, $C_1$–$C_5$ alkyl, $C_1$–$C_5$ alkoxy or halogen and M represents hydrogen, an alkaline- or alkaline earth-metal, or ammonium, characterised by hydrolysing one or more compounds of the formula (3)

(3)

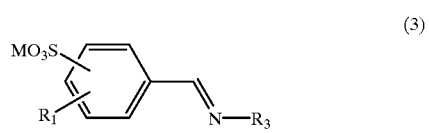

whereby $R_3$ represents phenyl, optionally substituted by $C_1$–$C_4$alkoxy, halogen or $SO_3M$, or $C_1$–$C_{12}$alkyl, and M and $R_1$ is defined as above, to produce one or more benzaldehydes of the formula:

(10)

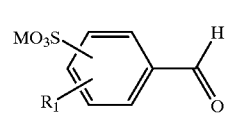

wherein M and $R_1$ are defined as above, which is reacted with a compound of formula (2)

(2)

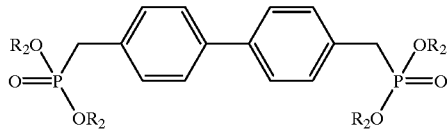

in which $R_2$ represents $C_1$–$C_5$alkyl, in an aprotic solvent and in the presence of a strong base.

9. A compound of the formula

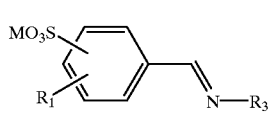
(3)

in which $R_3$ represents $C_1$ to $C_{12}$ alkyl or a radical of the formula

whereby $R_5$ is hydrogen, halogen or $C_1$ to $C_4$ alkoxy, and $R_1$ and M are defined as in claim 1.

10. A compound according to claim 9 of the formula

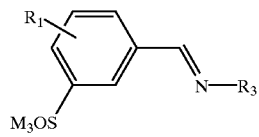
(8)

in which $R_3$ represents $C_1$ to $C_{12}$ alkyl or a radical of the formula

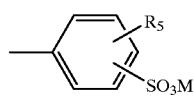
(9)

whereby $R_5$ is hydrogen, halogen or $C_1$ to $C_4$ alkoxy, and $R_1$ and M are as previously defined.

11. A compound according to claim 9 wherein $R_3$ is a $C_1$–$C_4$ alkyl group.

12. A process for the preparation of a compound according to claim 8 which comprises reacting a compound of formula:

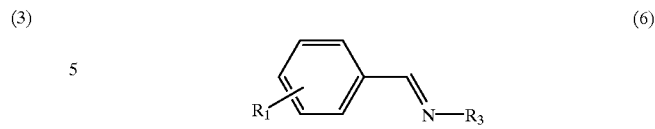
(6)

in which $R_1$ and $R_3$ are defined as in claim 8, with a sulphonating agent.

13. A compound of the formula:

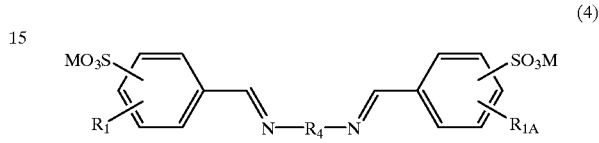
(4)

in which $R_1$, $R_{1A}$, $R_4$ and M are defined as in claim 1.

14. A process for the preparation of a compound according to claim 13 which comprises reacting of a compound of formula:

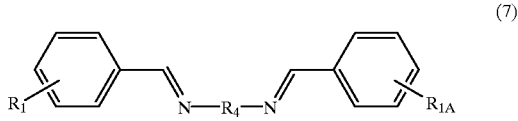
(7)

in which $R_1$, $R_{1A}$ and $R_4$ are defined there in with a sulphonating agent.

15. A process according to claim 12 in which the sulphonating agent is concentrated sulphuric acid, chlorosulphonic acid or oleum.

16. A process according to claim 14 in which the sulphonating agent is concentrated sulphuric acid, chlorosulphonic acid or oleum.

* * * * *